United States Patent
Shin et al.

(10) Patent No.: US 9,868,971 B2
(45) Date of Patent: Jan. 16, 2018

(54) METHOD FOR CONTROLLING LENGTH OF OVERHANG OF DOUBLE STRANDED DNA

(71) Applicant: ENZYNOMICS CO. LTD., Daejeon (KR)

(72) Inventors: Yong Keol Shin, Daejeon (KR); Yunil Suh, Daejeon (KR); Min Young Lee, Daejeon (KR); Ah Rong Jeong, Daejeon (KR)

(73) Assignee: ENZYNOMICS CO. LTD., Daejeon (KR)

( * ) Notice: Subject to any disclaimer, the term of this patent is extended or adjusted under 35 U.S.C. 154(b) by 116 days.

(21) Appl. No.: 14/766,281

(22) PCT Filed: Oct. 28, 2013

(86) PCT No.: PCT/KR2013/009611
§ 371 (c)(1),
(2) Date: Aug. 6, 2015

(87) PCT Pub. No.: WO2014/123293
PCT Pub. Date: Aug. 14, 2014

(65) Prior Publication Data
US 2015/0376672 A1    Dec. 31, 2015

(30) Foreign Application Priority Data
Feb. 8, 2013  (KR) .................. 10-2013-0014591

(51) Int. Cl.
| | | |
|---|---|---|
| *C12P 19/34* | (2006.01) |
| *C12N 15/10* | (2006.01) |
| *C12N 15/64* | (2006.01) |
| *C07H 21/04* | (2006.01) |
| *C12N 9/12* | (2006.01) |
| *C12N 15/65* | (2006.01) |

(52) U.S. Cl.
CPC .............. *C12P 19/34* (2013.01); *C07H 21/04* (2013.01); *C12N 9/12* (2013.01); *C12N 15/10* (2013.01); *C12N 15/64* (2013.01); *C12N 15/65* (2013.01)

(58) Field of Classification Search
CPC ........... C12P 19/34; C12N 9/12; C12N 15/10; C12N 15/64; C12N 15/65; C07H 21/04
See application file for complete search history.

(56) References Cited

U.S. PATENT DOCUMENTS

| | | | |
|---|---|---|---|
| 7,575,860 B2 | 8/2009 | Evans et al. | |
| 2008/0254525 A1* | 10/2008 | Zheng | C12N 9/1252 435/193 |
| 2012/0283144 A1 | 11/2012 | Kucera et al. | |

FOREIGN PATENT DOCUMENTS

WO     WO2007002031     *  1/2007

* cited by examiner

*Primary Examiner* — Alexander D Kim
(74) *Attorney, Agent, or Firm* — Vorys, Sater, Seymour & Pease LLP; Mih Suhn Koh (57) ABSTRACT

Disclosed are methods and kits for controlling the length of overhangs at the ends of double stranded DNA based on a competitive inhibition. Further provided are ligase-independent methods for joining the two ends of DNA strands using the same. The present methods efficiently control the overhangs of ds DNA. This user-controlled overhangs supply a tool for efficient ligation in a ligase independent way and can be advantageously used in DNA recombinant technology such as cloning gene or DNA fragments of interest or PCR products.

9 Claims, 7 Drawing Sheets

SEQUENCE LISTING

```
<160> NUMBER OF SEQ ID NOS: 2

<210> SEQ ID NO 1
<211> LENGTH: 52
<212> TYPE: DNA
<213> ORGANISM: Artificial Sequence
<220> FEATURE:
<223> OTHER INFORMATION: Substrate Strand_Forward strand 52 nt

<400> SEQUENCE: 1
cgaacaattc agcggcttta accggacgct cgacgccatt aataatgttt tc            52

<210> SEQ ID NO 2
<211> LENGTH: 52
<212> TYPE: DNA
<213> ORGANISM: Artificial Sequence
<220> FEATURE:
<223> OTHER INFORMATION: Substrate Strand_Reverse strand 52 nt

<400> SEQUENCE: 2
gaaaacatta ttaatggcgt cgagcgtccg gttaaagccg ctgaattgtt cg            52
```

METHOD FOR CONTROLLING LENGTH OF OVERHANG OF DOUBLE STRANDED DNA

The present application is a National Phase Application filed under 35 U.S.C. 371 as a national stage of PCT/KR2013/009611, filed Oct. 28, 2013, and claims the benefit of Korean Patent Application No. 2013-0014591, filed Feb. 8, 2013 in the Korean Intellectual Property Office, the disclosure of which are incorporated herein in its entirety.

The Sequence Listing submitted in text format (.txt) filed Aug. 6, 2015, named "SequenceListing.txt", created on Aug. 6, 2015, 670 bytes), is incorporated herein by reference.

BACKGROUND OF INVENTION

Field of the Invention

The present disclosure generally relates to control the length of overhangs present in double stranded DNAs.

Description of the Related Art

The process of joining the two ends of DNA strands is called ligation. DNA ligation is an essential step for cloning genes and DNA fragments or performing DNA recombinant technologies. One of the main factors that affect the efficiency of ligation is the type of the ends DNA strands have: blunt ends or cohesive ends with either 5' or 3' overhangs. Among them, the blunt and short cohesive ends tend to have a low efficiency.

The ligation may be performed either via a ligase dependent way in which the enzyme called ligase is used, or a ligase independent way. The latter is increasingly being used due to its short reaction time and high efficiency compared to the former.

US Patent Publication 2012-0283144 relates to a method to improve the efficiency of ligation and discloses the use of straight or branched diols or polyols with a molecular weight of 1000 Da or less in addition to ligases.

Examples of ligase independent methods include in vivo recombination based cloning and exonuclease based cloning. The latter is disclosed in U.S. Pat. No. 7,575,860. However, the methods employing exonucleases have a drawback that the ligation efficiency is heavily dependent on the overhang length. Thus there exist needs to develop ways to control the length of overhangs particularly for the application in the ligase independent cloning.

SUMMARY OF THE INVENTION

In the present disclosure, there is provided a method for generating an overhang with a desired length or for controlling overhang length at optimal length. Thus in one aspect there is provided a method for controlling overhang length of a double stranded DNA molecule at an optimal or desired length which comprises a step of providing a linear double stranded DNA; and a step of treating the ds DNA with a first DNA polymerase having a first exonuclease activity and a second DNA polymerase without a exonuclease activity or having a second exonuclease activity, by which the overhangs are generated and the length of which is at the desired range or level, wherein the first and the second polymerases are of identical or different types and the second exonuclease activity is weaker than the first exonuclease activity, wherein the activity of the first polymerase is competitively inhibited by the second polymerase, and wherein each end of the linear double stranded DNA is either of 5' overhang, 3' overhang or blunt-ended. In one embodiment, the exonuclease employed in the present methods has a 5'-3' directionality, or a 3'-5' directionality. In other embodiment, the first or second polymerase having the exonuclease activity has a proofreading activity. The examples include but are not limited to a Taq polymerase, a Phi29 DNA polymerase, a Pyrococcus-like polymerase, a Vent® DNA polymerase, a Pfx DNA polymerase, a Pfu DNA polymerase, an E. coli DNA polymerase, a T7 DNA polymerase, a T4 DNA polymerase, a Pyrococcus species GB-D DNA polymerase, a Thermococcus litoralis DNA polymerase, or a Thermococcus kodakaraensis KOD1 DNA polymerase, or mutant or modified forms thereof in which exonuclease activity is altered or changed. In other embodiment, the first and second polymerase includes polymerases may be of a viral origin including but not limited to a vaccinia virus, a fox virus, a herpes virus, an adenovirus, an iridovirus, a baculovirus, or from a single cell eukaryote including Saccharomyces cerevisiae.

In one embodiment, the first and second polymerases are combined or used in a molar ratio to produce an overhang length of 5 to 100 nt, for example in a molar ratio of about 1 to 100:1 to 100. The exact amount will vary depending on particular types and/or activity the DNA polymerases employed for the present methods.

In other aspect, there is also provided a ligase-independent DNA ligation, cloning kit used for the present methods, which comprise a first polymerase having an exonuclease activity and a second polymerase of identical or different type with its exonuclease activity lacking partially or completely such that the second exonuclease activity is weaker than the first exonuclease activity. The DNA polymerases in the present kit may be provided separately or combined in a molar ratio of ratio of 1 to 100: 1 to 100.

In still other aspect, there is also provided a method for joining two ends of ds DNA or cloning DNA, which comprises a step of providing at least two linear ds DNA molecules, each DNA molecule having at least one region located at either or both end thereof that is complementary to other region in the DNA molecules and a step of treating the ds DNA molecules with a first DNA polymerase having an exonuclease activity and a second DNA polymerase with no or partial exonuclease activity under a condition to produce overhangs of 5 to 100 nt in length at the complementary region, whereby the at least two ds DNA molecules are joined at the overhangs by complementarity, wherein the first and the second polymerases are of identical or different types and the second exonuclease activity is weaker than the first exonuclease activity, wherein the activity of the first polymerase is competitively inhibited by the second polymerase, and wherein each end of the linear double stranded DNA is either of 5' overhang, 3' overhang or blunt-ended. In one embodiment, one of the at least two linear ds DNA molecule is a cloning vector, and the method further comprises a step of transforming the joined molecule into a bacterial cell.

The foregoing summary is illustrative only and is not intended to be in any way limiting. Additional aspects and/or advantages of the invention will be set forth in part in the description which follows and, in part, will be obvious from the description, or may be learned by practice of the invention.

Advantageous Effects

The present disclosure provides efficient methods to control the overhangs of ds DNA. This user-controlled overhangs supply a tool for efficient ligation in a ligase independent way and can be advantageously used in DNA recombinant technology such as cloning gene or DNA fragment of interest or PCR products.

BRIEF DESCRIPTION OF THE DRAWINGS

These and/or other aspects and advantages of the invention will become apparent and more readily appreciated from the following description of the embodiments, taken in conjunction with the accompanying drawings of which:

In FIGS. 2A and 2B, the ds DNA substrate used is schematically represented at the top of each figure and the structures of the products generated are depicted on the right.

FIGS. 3A and 3B show that the exonuclease activity of a wild type polymerase can be controlled by a competitive inhibition with a mutant polymerase without exonuclease activity.

FIGS. 4A and 4B show that the cloning efficiency can be controlled using the present method.

DETAILED DESCRIPTION OF THE EMBODIMENTS

In the present disclosure, it has been found that during the generation of overhangs from the ends of ds linear DNA, the length of the overhang to be obtained can be controlled by a combined use of two kinds of DNA polymerases with differential exonuclease activity, i.e., one with exonuclease activity that is weaker or lower than the other in which they are acting competitively so that one with lower activity inhibits the function of the other having higher activity.

Figure 5:
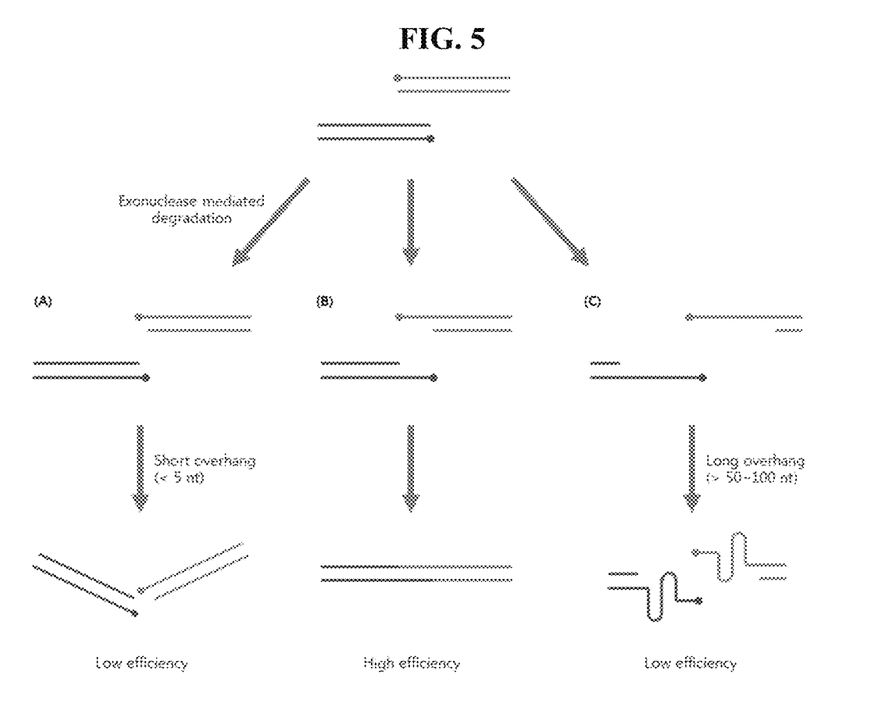
FIG. 5 is a schematic diagram depicting the efficiency of the ligation depending on the length of overhangs involved.

In a ligase-independent method of joining two ends of ds DNAs, it is important that 5' or 3' overhangs with optimal length are generated, which is done using a DNA polymerase having 3'->5' exonuclease activity or 5'->3' exonuclease respectively. When the exonuclease activity, for example 3'->5' exonuclease activity is low or not enough, 5' ssDNA (single stranded DNA) or overhangs with not more than 5 bases in length are generated. This results in poor annealing between the complementary regions of the overhangs leading to a low ligation efficiency as depicted in FIG. 5A. On the contrary, a strong or enough 3'->5' exonuclease activity leads to a longer 5' ssDNA at the end of ds DNA. The longer single stranded region may allow the formation of secondary structures leading to low ligation efficiency as depicted in FIG. 5C. Therefore, it is imperative to obtain overhangs with optimal length for an efficient and successful ligation or cloning. The optimal length allows a stable annealing between the complementary regions without forming secondary structures (Refer to FIG. 5B).

As used herein the term ligation in relation to DNA refers to joining two ends of dsDNA of the same or different molecules. The terms ligation and joining (or join) are used interchangeably.

As used herein the term double stranded DNA (dsDNA) refers to oligonucleotides or polynucleotides having 3' overhang, 5' overhang or blunt ends and composed of two single strands all or part of which are complementary to each other, and thus dsDNA may contain a single stranded region at the ends and may be synthetic or natural origin derived from cells or tissues. In one embodiment, dsDNA is a product of PCR (Polymerase Chain Reaction) or fragments generated from genomic DNA or plasmids or vectors by a physical or enzyme treatment thereof.

As used herein the term overhang refers to the single stranded region of ds DNA at the end thereof and is either of type 5' or 3' due to the inherent directionality of DNA. The overhangs are generally generated in various lengths by treating dsDNA with restriction enzymes or exonucleases and/or by the addition of appropriate dNTPs (dATP, dTTP, dCTP, dGTP).

In one aspect of the present disclosure, there are provided methods that can control the length of the overhangs of ds DNAs at a desired or optimal length or generate the overhangs whose lengths can be controlled at a desired or optimal length. The methods are based on the competitive inhibition between two DNA polymerases having different exonuclease activity. In one embodiment the present method comprises providing a linear double stranded DNA; and treating the DNA with a first DNA polymerase having an first exonuclease activity and a second DNA polymerase without exonuclease activity or having a second exonuclease activity, wherein the first and the second DNA polymerase are of the identical or different types and the second exonuclease is partially active compared to the wild-type and weaker than the first exonuclease activity and wherein the ends of the ds DNA at the start of the reaction are either of 5' overhang, 3' overhang or blunt-ended.

The DNA polymerases which may be used for the present disclosure may be of any kinds having 3'->5' or 5'->3' exonuclease activities and/or being able to joining the entirely or partially two complementary ends of DNA. Thus polymerases with various origins may be used. The first and second polymerases may be of the same or different type or origins. For example as a first polymerase, a wild type Taq polymerase having exonuclease activity and as a second polymerase, a mutant Taq polymerase lacking exonuclease activity partially or entirely may be employed.

In one embodiment, thermophilic or mesophilic polymerases of various origins are used. For example, polymerases which may be used for the present disclosure include but are not limited to a Taq DNA polymerase from *Thermus* sp. such as *Thermus aquaticus*, a Phi29 DNA polymerase, a high fidelity DNA polymerase (for example *Pyrococcus*-like polymerase fused with a processivity enhancing domain from New England Biolabs, USA), a polymerase from *Thermococcus litoralis* such as Vent® DNA polymerase from New England Biolabs, a Pfx DNA polymerase from *Pyrococcus* sp. such as Platinum® Pfx DNA polymersase from Life technologies, USA, a Pfu DNA polymerase from *Pyrococus furious*, a *E. coli* DNA polymerase, a T7 DNA polymerase, a T4 DNA polymerase, a *Pyrococcus* sp. GB-D DNA polymerase, or *Thermococcus kodakaraensis* KOD1 DNA polymerase such as KOD from Toyobo, Japan. Further polymerases of various origins are used for the present disclosure and include ones from a vaccinia virus, a fox virus, a herpes virus, an adenovirus, an iridovirus, a baculovirus, or from a single cell eukaryotes including *Saccharomyces cerevisiae*.

In one embodiment, DNA polymerases with a proof reading activity or exonuclease activity, i.e., 3'->5' exonuclease activity are used. Any kinds or types of such polymerases may be used for the present disclosure given that it is functional within the present disclosure. These polymerases with a proof reading activity or exonuclease activity such as Pfu DNA polymerase can eliminate erroneously incorporated nucleotides and replace them with a correct base, which usually depends on the concentration of dNTPs in the reaction mixture. That is, when enough dNTPs are present in the reaction mixture, they perform mainly as a polymerase, and when dNTPs are present under optimal concentration they perform as an exonuclease and remove the bases from the 3' or 5' end. The optimal concentration means the amount of dNTP under which the polymerase activity prevails over the exonuclease activity.

The ends of ds DNA in the present disclosure are either of 5' overhang, 3' overhang or blunt-ended.

Figure 1:
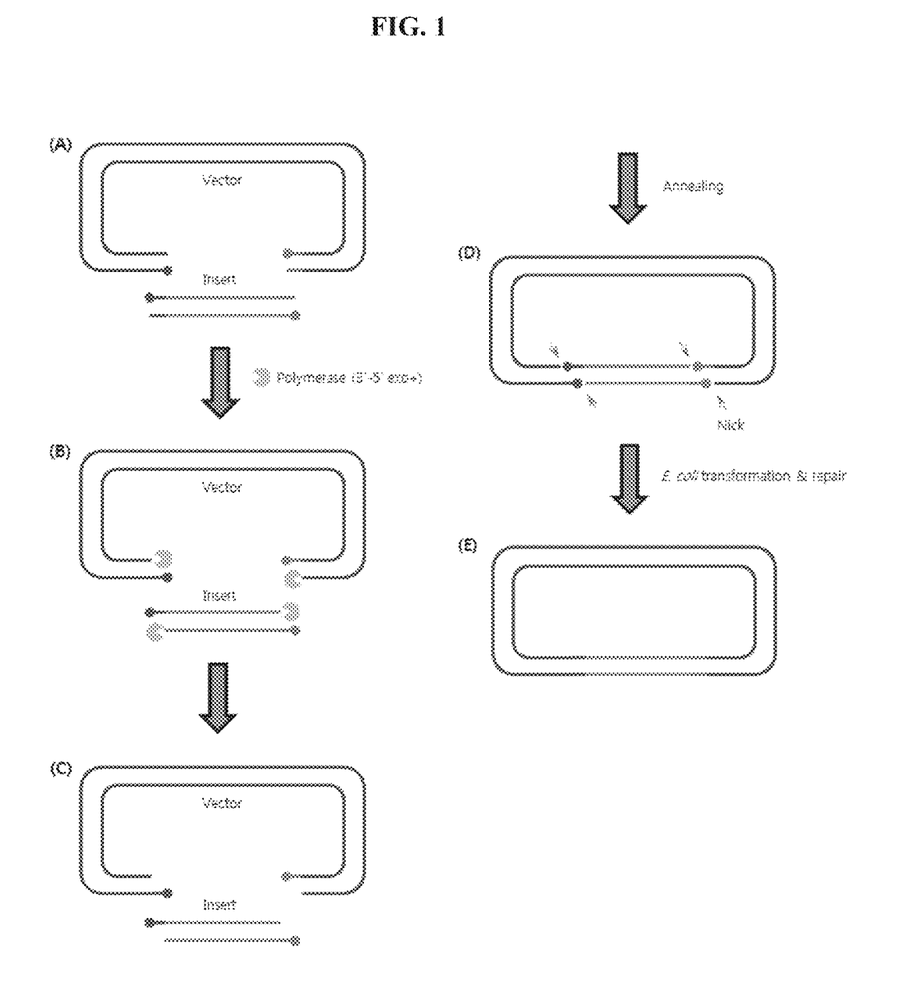
FIG. 1 is a schematic diagram of a DNA ligation process using a polymerase having exonuclease activity.
Figure 2A:
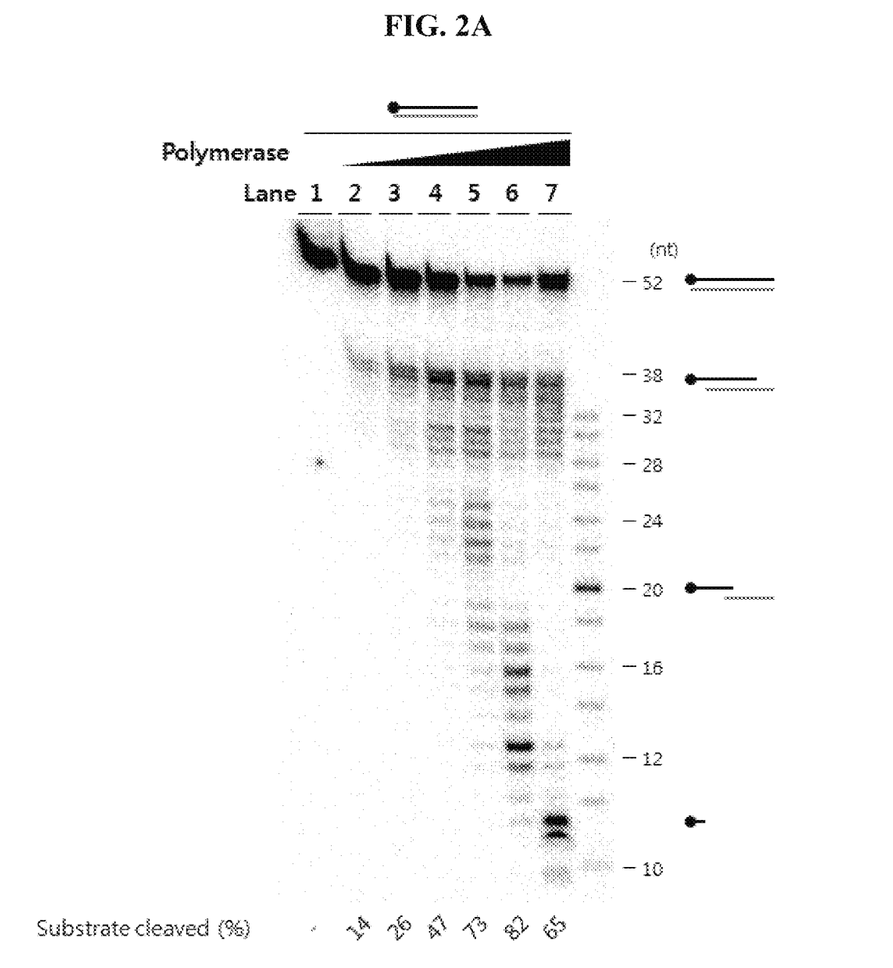
FIG. 2A is an electrophoresis result of ds DNA treated with various amounts of polymerase having exonuclease activity showing that the amount and length of ds DNA digested increased according to the amounts of polymerase used, in which KOD polymerase was used and its 3' exonuclease activity was measured.
Figure 2B:
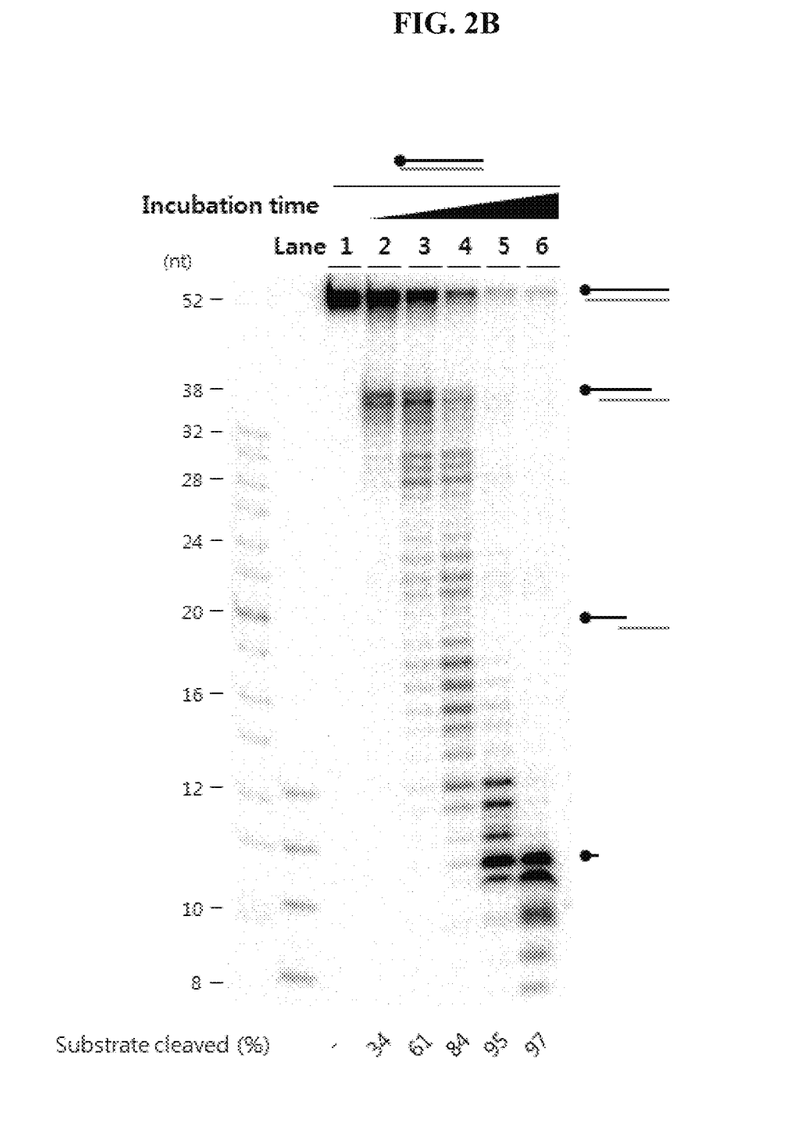
FIG. 2B is an electrophoresis result of ds DNA treated for various time periods with a same amount of polymerase having exonuclease activity showing that the amount and length of ds DNA digested increased according to the incubation time, in which KOD polymerase was used and its 3' exonuclease activity was measured.

As shown in FIG. 2, the 3'->5' exonuclease processively removes nucleotides from the 3' end resulting in the generation of mixtures of overhangs with various sizes ranging from short to long rather than the generation of overhangs homogenous in size. Thus by increasing the amount of polymerase used in the reaction, the ligation efficiency may become low due to the generation of long overhangs.

According to the present methods, the length of overhangs can be controlled or obtained at a desired or optimal length by employing two polymerases different in their exonuclease activities, one with exonuclease activity for example at the wild type level and the other polymerase which lacks exonuclease activity partially or entirely. In the present methods, the two polymerases control the length of overhangs by a competitive inhibition therebetween. The optimal or desired length is determined by the ratio of the two DNA polymerases.

Polymerases lacking exonuclease activity partially or entirely which may be used for the present disclosure are not limited to a particular type as long as it is functional within the present disclosure and include those known in the related art. Examples include but are not limited to an exo-mutant polymerase in which exonuclease domain is deleted, or a mutant KOD polymerase in which amino acid residue 210 is substituted from asparagine to aspartic acid.

As described hereinbefore, in the present methods when two DNA polymerases one with exonuclease activity and the other without or less exonuclease activity than the other are used together, the mutant DNA polymerase binds to the substrate without catalyzing the removal of bases thus inhibiting the activity of the wild type polymerase in the same reaction mixture. In this way the length of the overhangs can be controlled at a certain level and the optimal or desired length is determined by the ratio of the two DNA polymerases.

The optimal or desired length is mainly determined by the ratio of the two DNA polymerases. In the present disclosure, the polymerase with a full or wild type level of exonuclease activity and the mutant, i.e., exo⁻ polymerase in which all or part of its exonuclease function such as 3'->5' exo is removed may be combined or used in various ratios according to the desired length of overhangs. The present methods can be advantageously used for a ligase-independent DNA joining process, for which the length of overhangs are generated and controlled to provide a complementarity enough for allowing stable annealing while no or less secondary structures are formed. In one embodiment of the present disclosure, the length of overhangs are for example about 5 nt to 100 nt long, or about 5 nt to about 50 nt long. When the length of overhang is less than 5 nt long, the annealing may become unsuccessful or inefficient due to the weak binding force from the low complementarity (Refer to FIG. 6A). Further when the length of overhang is more than 100 nt long, the annealing may become unsuccessful or inefficient due to the secondary structures formed in the overhangs (Refer to FIG. 6C).

To produce or generate the overhangs meeting the conditions as described above, the ratio of two polymerases employed for example such as wild type polymerase with a full exonuclease activity and exo⁻ mutant polymerase lacking 3'->5' exonuclease activity may be determined or adjusted according to the desired length of overhangs to be produced. Also considered are factors such as particular types of polymerases employed, the levels of 3'->5' exonuclease activity of the mutant polymerase, and other reaction conditions and the like. In one embodiment, the first and second polymerases are provided in a molar ratio of about 1 to 100:1 to 100. In other embodiment, a KOD DNA polymerase and a mutant KOD in which the exonuclease activity is completely removed are used in a molar ratio of about 1:4 for the generation of 14 nt long overhang. In this case 5' overhangs are generated due to the 5'->3' exonuclease activity. In the process, it is not necessary that the length of all the overhangs involved in the annealing may not be of the same size. Also the complementarity may not be present over the entire length of the overhangs involved in the annealing. Thus gaps may be present after the annealing which is filled in during the following amplification step in cells such as bacteria.

The reaction conditions under which the DNA polymerases are functional are known in the related art and are readily appreciated by the ordinary person in the related art in consideration of the purpose or characteristics of the present disclosure.

For example, most of the polymerases harboring exonuclease activity require a cation for the proper function. The cations such as magnesium or manganese may be used but are not limited thereto. The cations are used in an amount enough to produce DNA amplification or polymerization or to produce exonuclease activity. The reaction time may vary depending on factors such as particular types of polymerases or cations employed or reaction temperature. Appropriate reaction time ranges from about 1 min to about 100 minutes but are not limited thereto.

The reaction temperatures are mainly determined by the type of polymerase employed. The upper limit of the reaction temperature is determined by the stability of the polymerase employed and the lower limit is determined by the activity of the polymerase employed. For example, for thermophilic DNA polymerases the reaction temperature ranges from −2° C. to 105° C., particularly 4° C. to 95° C. In one embodiment, reaction temperature ranges from 10° C. to 50° C.

Also embodied in the present disclosure are kits and compositions for performing a ligase-independent ligation, cloning or joining of two ds DNAs, which comprise a first DNA polymerase having a first exonuclease activity and a second DNA polymerase of the identical or different type with no or partial exonuclease activity so that the second DNA polymerase has a exonuclease activity lower or weaker than the first one. For the components which may be included in the present kits and compositions, the description hereinbefore may be referred. The polymerases included in the kits are provided separately or combined as at least one mixture of the two polymerases in appropriate molar ratios. When the polymerases are provided separately, they may be mixed before use in an appropriate ratio for a desired length of overhang. The kits may further comprise an instruction or manual for using the kit.

Also embodied in the present disclosure are methods for joining the two ends of double stranded DNA. In one embodiment the present method includes providing one or at least two linear ds DNA strands, each having at least a region at the end of the DNA that is complementary to other region at the end of the other DNA molecules; and treating and incubating the ds DNA strands with a first polymerase having an first exonuclease activity and a second polymerase having a second exonuclease activity, under a condition to produce overhangs of 5 to 100 nt in length, whereby the at least two ds DNA molecules are joined at the overhangs by complementarity thus one linear DNA molecule becomes circular or the two linear ds DNA strands are combined into one molecule, wherein the first and the second polymerase are of the identical or different types and the second exonuclease activity is weaker than the first exonuclease activity, lacking completely or partially and wherein the ends of the ds DNA at the beginning of the reaction are either of 5' overhang, 3' overhang or blunt-ended.

In one embodiment, the present joining methods are used for DNA cloning, in which case, two ds DNA strands are used and one of the ds DNA strand is a cloning vector and the other strand is an insert and the method further comprises a transformation step to introduce the ligated products into bacterial or eukaryotic cells for amplification. The term vector as used herein refers to a DNA molecule being able to be self-replicated in eukaryotes and/or prokaryotes and interchangeably used with plasmid, recombination vector, cloning vector, or expression vector. They are used as a carrier to deliver genes or nucleic acid fragment of interest to cells. The vectors generally comprise an origin of replication for eukaryotes and prokaryotes, a selection marker(s) conferring resistance to a particular material or condition, a promoter for transcription in eukaryotes and/or prokaryotes and a signal sequence for translation without limitation.

The methods for transforming bacterial or eukaryotic cells are known in the art. Examples include but are not limited to a calcium phosphate method, an electroporation and a shot gun method, which will be readily appreciated and selected by the person of ordinary skill in the related art.

In one embodiment, the polymerases which may be employed for the present methods may be referred to the description hereinbefore.

The ds DNA molecules which may be used for the present methods are vectors or genes or oligonucleotides or DNA fragments of synthetic or natural origin or amplified product such as PCR products. The circular DNA may be linearized before use using the appropriate methods known in the related art.

The at least two ds DNA molecules employed in the present disclosure includes at least one end complementary to the end of the other strands. The complementarity may be ones naturally present or may be appropriately introduced. The complementarity may be generated by methods known in the art including such as by the use of restriction enzymes, by PCR by using primers harboring particular sequence of interest or by inverse PCR and the like.

When the at least two linear ds DNA strands each having at least one end complementary to the end of the other strand are treated with two polymerases having different exonuclease activity as described above in the absence of dNTP or dNTP under the concentration which prefers the exonuclease activity over the polymerase activity, overhangs are generated at the ends of each of the two strands and the two DNA strands are connected or joined at the overhangs generated, which may contain gaps. The gaps are then filled during the amplification in bacterial cells to which the ligated products are introduced by a process called transformation.

The types and ratios of DNA polymerases employed and reaction conditions are as described hereinbefore and after.

The present disclosure is further explained in more detail with reference to the following examples. These examples, however, should not be interpreted as limiting the scope of the present invention in any manner.

EXAMPLES

Example 1

Control of the Length of 5' Overhang by a Competitive Inhibition

The experiments were performed as below. As a DNA polymerase, wild type KOD polymerase from *Thermococcus kodakaraensis* KOD1 having 3'->5' exonuclease activity was prepared as described (Nishioka M, et al., 2001. Long and accurate PCR with a mixture of KOD DNA polymerase and its exonuclease deficient mutant enzyme. J Biotechnol. 2001 Jun. 15; 88(2):141-9). Further as a mutant DNA polymerase, the same KOD as above except that the exonuclease activity was inactivated by asparagine to aspartic acid substitution at amino acid reside 210, N210D were prepared as described (Nishioka M, et al., 2001. Long and accurate PCR with a mixture of KOD DNA polymerase and its exonuclease deficient mutant enzyme. J Biotechnol. 2001 Jun. 15; 88(2):141-9.)

For a competitive inhibition assays, the wild type KOD DNA polymerase was used at a fixed amount of 10 fmol with increasing amounts of mutant KOD DNA polymerase from 5 fmol to 40 fmol with 10 and 20 fmols in between at 37° C. for 15 min. The DNA fragments (substrate) used were chemically synthesized (Genotech. Korea) and have the following sequence: Forward strand SEQ ID NO: 1 5'-CGAACAATTCAGCGGCTTTAACCGGACGCTC- GACGCCATTAATAAT GTTTTC-3' 52 nt, Reverse strand SEQ ID NO: 2 5'-GAAAACATTATTAATGGCGTC-GAGCGTCCGGTTAAAGCCGCTGAAT TGTTCG-3' 52 nt. Then the forward strands were labelled at their 5'end using [$^{32}$P] and then mixed with the reverse strands and incubated at 100° C. for 5 min for denaturation. The mixture was allowed to cool at RT to form ds DNA by annealing, which have a complete complementarity and thus are blunt-ended. The buffer included 50 mM Tris-HCl pH 7.9, 70 mM NaCl, 0.1% Triton X-100, 5 mM MgCl2, 0.01 mg/ml BSA, and 1 mM dithiothreitol.

Figure 3:
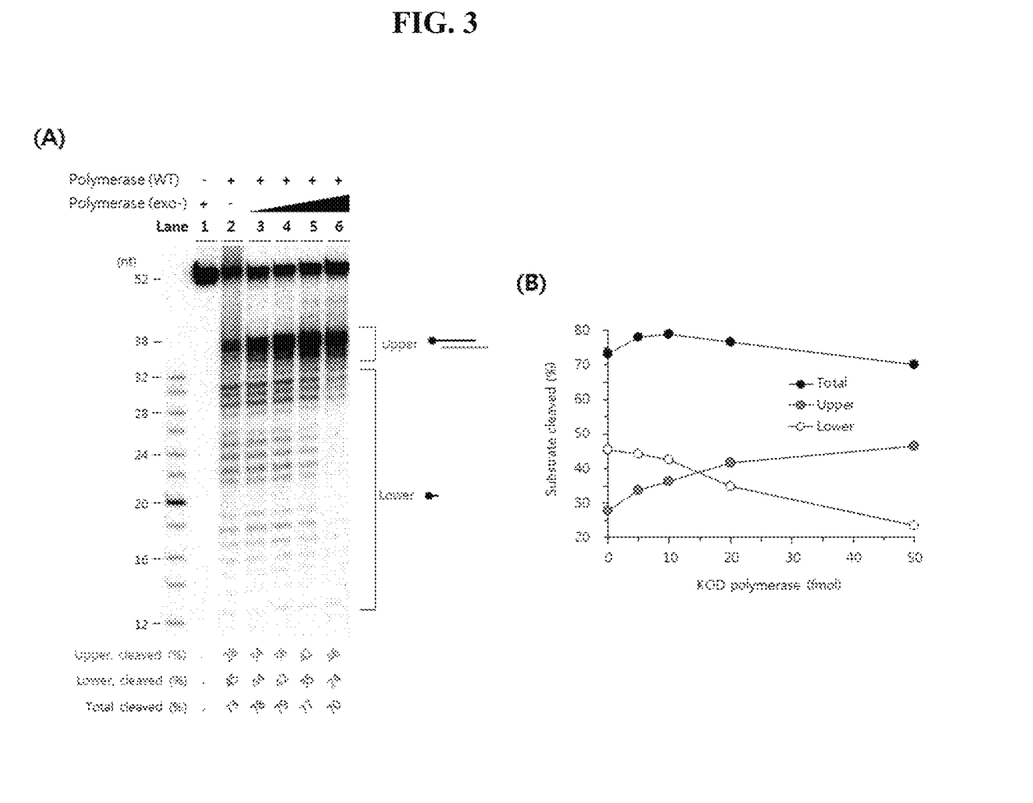
FIG. 3A is an electrophoresis result of ds DNA treated with a fixed amount of wild type KOD polymerase and an increasing amount of mutant KOD from 1:0 to 1:4 molar ratio, in which the upper denotes the products greater than 14 nt, and the lower denotes the products not greater than 14 nt and the amount of substrate digested was measured in two groups of the upper and lower.
FIG. 3B is a graph plotting the quantification result of FIG. 3A.

Results are shown in FIG. 3, which shows that only 28% of the strands were found to have a 14 nt long overhang (upper products, 38 nt) when wild type KOD was used alone. However, with a combined use of wild type and exo-mutant KOD, the value increased about 2 times upto 48%.

In contrast, the amount of products in which 15 nt to 40 nt were removed from the 3' end (15 nt to 40 nt long overhang, lower product, 12-32 nt) were reduced about 50% in the combined use of wild type and exo-mutant DNA polymerase in comparison to the results using KOD alone.

In all the reactions performed, it was found that the addition of exo-mutant KOD polymerase does not affect the total amount of products generated (FIG. 3A, total cleaved).

These results indicate that the optimum length of overhangs can be obtained by the combined use of a wild type DNA polymerase such as KOD and a mutant polymerase such as exo-KOD in which the mutant polymerase competitively inhibits the exonuclease activity or function of the wild type polymerase in the absence of dNTP.

Example 2

Improvement of Cloning Efficiency by a Competitive Inhibition

Below experiments were performed to test whether the cloning efficiency can be improved using the DNA fragments with controlled length of overhangs as Example 1.

A 0.5 pmol of wild type KOD polymerase as described in Example 1 was combined with mutant exo-KOD polymerase in a molar ratio of 1:0, 1:1 and 1:4. The mixture was used for a ligation reaction. For the ligation, 40 ng of a 2 kb PCR product having blunt ends and 80 ng of pUC19 vector linearized with Sma I was incubated at 37° C. for 15 min. The same buffer as described in Example 1 was used.

The ligation products were then introduced into *E. coli* DH5 alpha by a calcium phosphate method and the transformed cells were then spread onto a plate containing ampicillin and incubated at 37° C. until the colonies were formed.

Figure 4A:
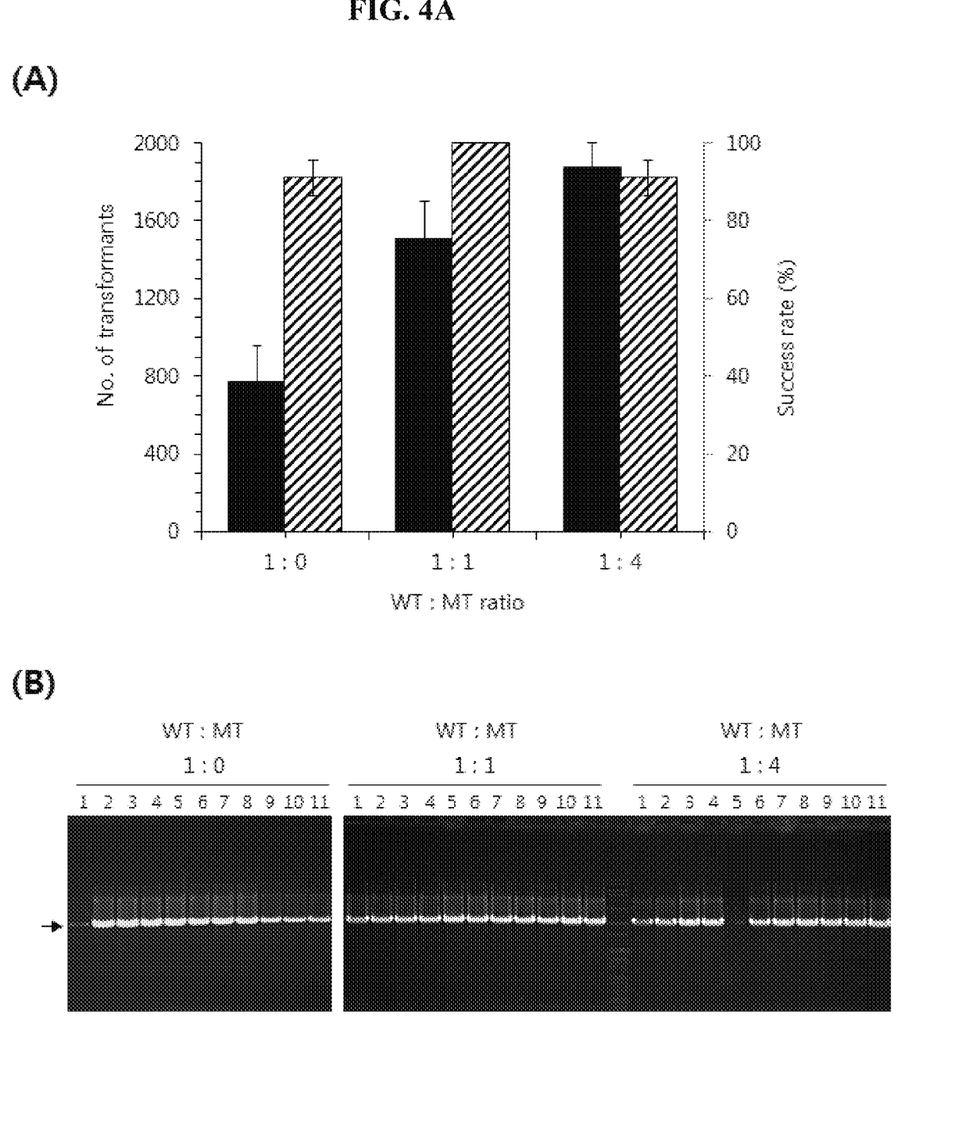
FIG. 4A is a graph showing the cloning efficiency measured in which an 1 kb insert was ligated into a 3 kb vector in the presence of a fixed amount of wild type polymerase with an increasing amount of mutant polymerase from 1:0 to 1:4 in molar ratio. In the graph, the number of colonies formed was indicated as a black bar on the left among which the colonies harboring the vector with the insert were indicated as a slashed bar on the right.
Figure 4B:
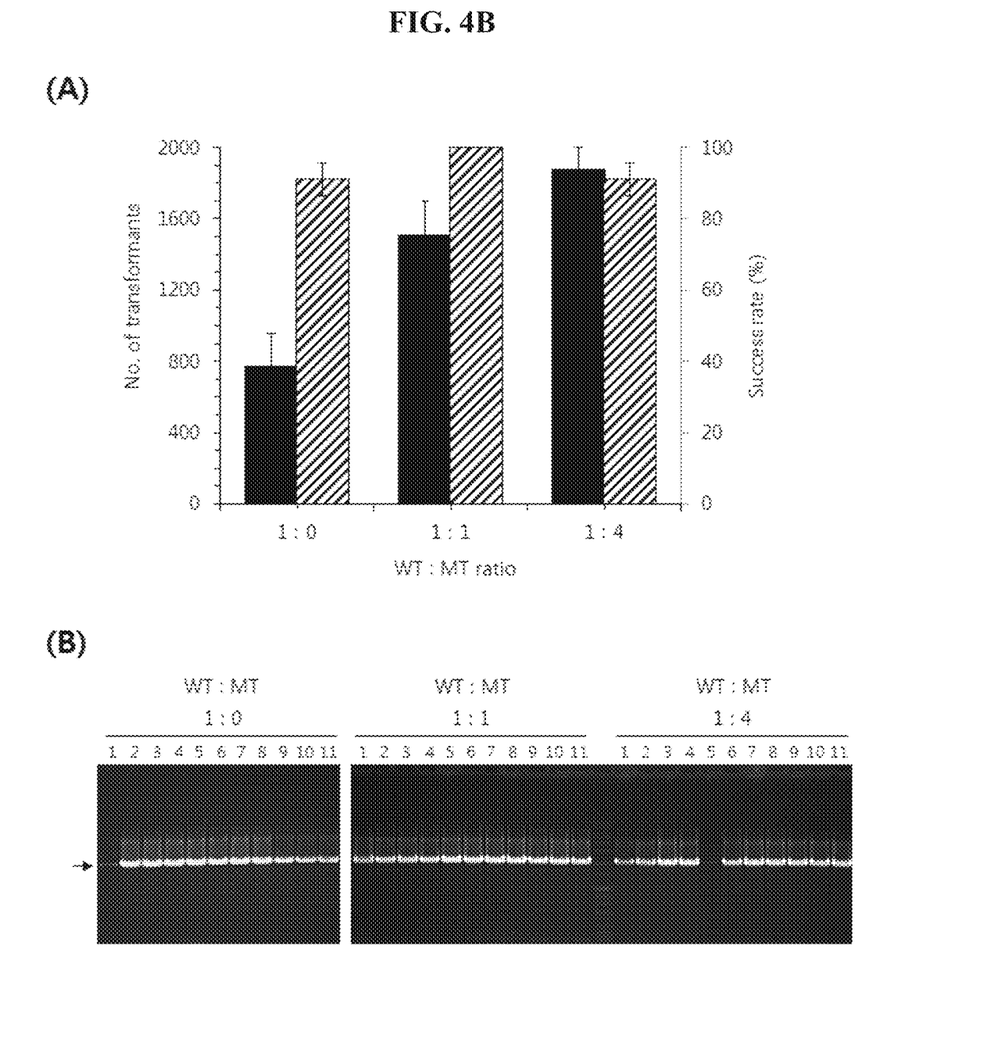
FIG. 4B is an electrophoresis result of the PCR products performed on the colonies as generated in FIG. 4A to confirm that the ligation was successful in which the arrow indicates the expected products.

Results are shown in FIG. 4, which shows that the number of colonies was increased upto 2 times as the molar ratio of wile type KOD and mutant KOD was increased from 1:0 to 1:4. Also the success rate of the cloning was found to be at least 90% in all cases. Further when the same experiments were done at different temperatures of 4° C., 25° C., 37° C. and 50° C., 2-3 times more colonies were formed at 37° C. compared to other temperatures tested.

These results indicate that the cloning efficiency can be improved by controlling the 5' overhang at optimal length by the present methods Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

What is claimed is:

1. A method of controlling overhang length of a double strand DNA comprising:
    providing a linear double strand DNA (ds DNA); and
    treating the ds DNA with a first DNA polymerase having a 3'-5' exonuclease activity and a second DNA polymerase without a 3'-5' exonuclease activity in the absence of dNTPs,
    wherein the 3'-5' exonuclease activity of the first polymerase is competitively inhibited by the second DNA polymerase,
    and wherein each end of the linear ds DNA is either of 5' overhang, 3' overhang or blunt-ended.

2. The method of claim 1, wherein the first polymerase includes a Taq polymerase, a Phi29 DNA polymerase, a *Pyrococcus*-like polymerase, a Vent® DNA polymerase, a Pfx DNA polymerase, a Pfu DNA polymerase, an *E. coli* DNA polymerase, a T7 DNA polymerase, a T4 DNA polymerase, a *Pyrococcus* species GB-D DNA polymerase, a *Thermococcus litoralis* DNA polymerase, or a *Thermococcus kodakaraensis* KOD1 DNA polymerase, and the second polymerase includes a mutant form thereof without exonuclease activity, or a Taq polymerase.

3. The method of claim 1, wherein the first and second polymerase includes polymerases of viral origin including a vaccinia virus, a pox virus, a herpes virus, an adenovirus, an iridovirus, a baculovirus, or from a single cell eukaryote including *Saccharomyces cerevisiae*.

4. The method of claim 1, wherein the first and second polymerase are used at a molar ratio to produce an overhang of 5 to 100 nt in length.

5. The method of claim 1, wherein the first and second polymerase are used at a molar ratio of 1 to 100:1 to 100.

6. The method of claim 1, wherein the treatment is performed at 4° C. to 72° C. for 1 to 60 minutes.

7. A method of joining two ends of double strand DNA (ds DNA), comprising:

providing at least two linear ds DNA molecules, each DNA molecule having at least one region located at either or both end(s) thereof that is complementary to other region in the DNA molecules, wherein each end of the two linear ds DNA is either of 5' overhang, 3' overhang or blunt-ended; and treating the at least two ds DNA molecules with a first DNA polymerase having an 3'-5' exonuclease activity and a second DNA polymerase with no 3'-5' exonuclease activity in the absence of dNTPs under a condition to produce overhangs of 5 to 100 nucleotide (nt) in length at the complementary region, whereby the at least two linear ds DNA molecules treated are joined at the produced overhangs by complementarity, wherein the 3'-5' exonuclease activity of the first polymerase is competitively inhibited by the second DNA polymerase.

8. The method of claim 7, wherein one of the at least two linear ds DNA molecule is a cloning vector, and further comprising transforming the joined molecule into a bacterial cell.

9. The method of claim 7, wherein the first and second polymerases are used in a molar ratio of 1 to 100:1 to 100.

* * * * *